US00PP09413P

United States Patent [19]

McGredy

[11] Patent Number: Plant 9,413

[45] Date of Patent: Jan. 2, 1996

[54] MINIATURE ROSE PLANT NAMED 'MACCRICKE'

[76] Inventor: Samuel D. McGredy, 130 B Beach Road, Castor Bay, Auckland 9, New Zealand

[21] Appl. No.: 315,900

[22] Filed: Sep. 30, 1994

[51] Int. Cl.[6] ..... A01H 5/00

[52] U.S. Cl. ..... Plt./7.1

[58] Field of Search ..... Plt./7.1, 10

*Primary Examiner*—Howard J. Locker

[57] ABSTRACT

A new and almost continuously and profusely blooming rose plant, of the miniature class, having conspicuous, open-faced flowers with petals gently rounded in shape but having a minute point on the centerline; such petals of deep pink coloring with a white margin on the outer edge; the long lasting flowers being pleasantly highlighted by their placement over healthy and deep green foliage on a bushy, upright, vigorously growing plant.

1 Drawing Sheet

BACKGROUND OF THE INVENTION

The present invention relates to a new and distinct variety of rose plant of the miniature rose class which was originated by me by crossing, as the seed parent, 'Sea Breeze' and as pollen parent the rose plant known as 'Little Artist'. Upon recognition of the attributes of this plant within the progeny of the stated cross, it was elected for further testing and observation. Upon recognition that this plant was novel and expressed numerous superior and desirable traits as described below, the plant of this application was assigned an international recognition name of 'Maccricke'. This plant has been asexually reproduced by me or under my direction by cuttings and by budding in Washington County, Oreg. Such asexual reproduction has conclusively shown that all distinguishing characteristics of this plant come true to form, are firmly fixed, and are faithfully transmitted through succeeding propagations.

Specimens described below were grown in Washington County, Oreg.

SUMMARY OF THE INVENTION

The new plant of this invention contains a number of outstanding attributes in combination which set it apart from all other plants of the miniature rose market class. Such characteristics may be summarized as follows:

A new and conspicuously attractive flower having numerous rich, deep pink petals.

Petals of gently rounded shape of deep pink coloring with a white margin on the outer edge of the petals, having a small point at the center of the rounded apex of margin.

Open faced flowers which open to a substantially flat form, with petals slightly cupped outward.

Flowers being pleasantly highlighted above lush, dense foliage which is healthy in appearance.

A bushy plant which is highly remontant and blooms almost continuosuly and profusely.

Flowers formed singly or in sprays placed over a healthy and dense crop of glossy, deep green foliage on an upright, compact, but vigorously growing well branched plant.

BOTANICAL DESCRIPTION OF THE PLANT

The following is detailed description of my new variety, with color terminology in accordance with the Royal Horticultural Society Color Chart (RHSCC). The terminology used in color description herein refers to plate numbers in the aforementioned color chart. "135C" is plate 135C of the Royal Horticultural Society Color Chart.

Parentage:

*Seed parent.*—Sea Breeze.

*Pollen parent.*—Little Artist.

Class: Miniature.

The following observations are made of specimens grown out doors in Washington County, Oreg. during June. The color photograph illustrates the cultivar, including buds, flowers, and foliage. The colors depicted are as accurate as is reasonably possible to attain in color illustrations of this type.

FLOWER

Blooming habit: Nearly continuous, with blooms occurring both singly and in flushes.

A. Bud:

(1) *Size.*—About 1 cm. long buds with no foliaceous appendages to the buds.

(2) *Form.*— Globular.

(3) *Color.*—The reverse of the bud is deep pink 57C.

(4) *Sepals.*—Permanent, spear shaped, reflexed color green (137A).

(5) *Peduncle.*—Length — about 2 cm. Aspect —straight. Strength —erect, but some arching. Color —near 137A green.

B. Bloom:

(1) *Size.*—When fully expanded — about 3 cm.

(2) *Borne.*—Singly and in sprays of 4 to 7 blooms.

(3) *Form.*—Flat, slightly cupped outward.

(4) *Petalage.*—About 65 under normal conditions.

(5) *Color.*—Deep pink (57C) on inner and outer sides of petals with white at the outer margins of the petals.

C. Petals:

(1) *Texture.*—Moderately thick and of good substance.

(2) *Appearance.*—Velvety, both inside and outside.

(3) *Form.*—The bloom has imbricated form with normal depth. The petals are pointed.

(4) *Arrangement.*—Regularly arranged.

(5) *Petaloids in center.*—Medium, surrounding center.

(6) *Persistence.*—Petals drop off cleanly.

(7) *Fragrance.*—None.

(8) *Lasting quality.*—Blooms last about five days cut or on the bush.

REPRODUCTIVE ORGANS

A. Stamens, filaments and anthers:

(1) *Arrangement.*—Regularly arranged stamens around low pistils.

(2) *Color.*—Medium yellow, aging to darker yellow.

B. Pollen:

*Color.*—Medium yellow.

C. Styles: Long, even length — introrse.

D. Stigmas:

*Color.*—Medium yellow.

E. Hips: Does not set hips.

F. Sepals: Permanent, spear shaped, reflexed.

PLANT

A. Form: Medium height, bushy.

B. Growth: Uniform branching to about 2 feet tall with good vigor. Pinching induces further branching.

C. Foliage: Compound 5 leaflets (most often).

(1) *Size.*—1½ cm leaflets.

(2) *Quantity.*—Abundant.

(3) *Color.*—New foliage 135C green maturing to 137B green.

(4) *Shape.*—Oval pointed supported by short petiolule.

(5) *Texture.*—Glossy.

(6) *Edge.*—Serrated.

(7) *Serration.*—Very fine, saw shaped.

(8) *Leaf stem.*—Color — green 135C.

(9) *Stipules.*—Lightly bearded, and ¾ cm long.

(10) *Rachis.*—Green color, medium 1 cm., upper side grooved.

(11) *Resistance to disease.*—Blackspot — average. Mildew — average. Rust — average.

D. Wood:

(1) *New wood.*—Color — light green 137B — smooth.

(2) *Old wood.*—Color — green 1367B. Bark — smooth with sturdy growth, 3 cm. internodes.

E. Thorns:

*Quantity.*—Both main stalk and laterals from stalk are average.

*Form.*—Dilated at base and declining.

*Length.*—⅓ cm.

*Color.*—red-toned 178A changing to brown at maturity.

*Position.*—Ordinary.

*Prickles.*—Average.

F. Winter hardiness: Requires ordinary protection in extreme climates.

I claim the following:

1. A new and distinct variety of miniature rose plant substantially as described and illustrated, which is particularly characterized by being easy to propagate; vigorous, hardy, bushy and upright habit; having blooms borne singly or in sprays from 4 to 7 which open slowly to a flat form with cup shaped petals of deep pink coloring with a slight white margin at the outer edges; and, the flowers being produced in abundance covering much of the healthy green foliage.

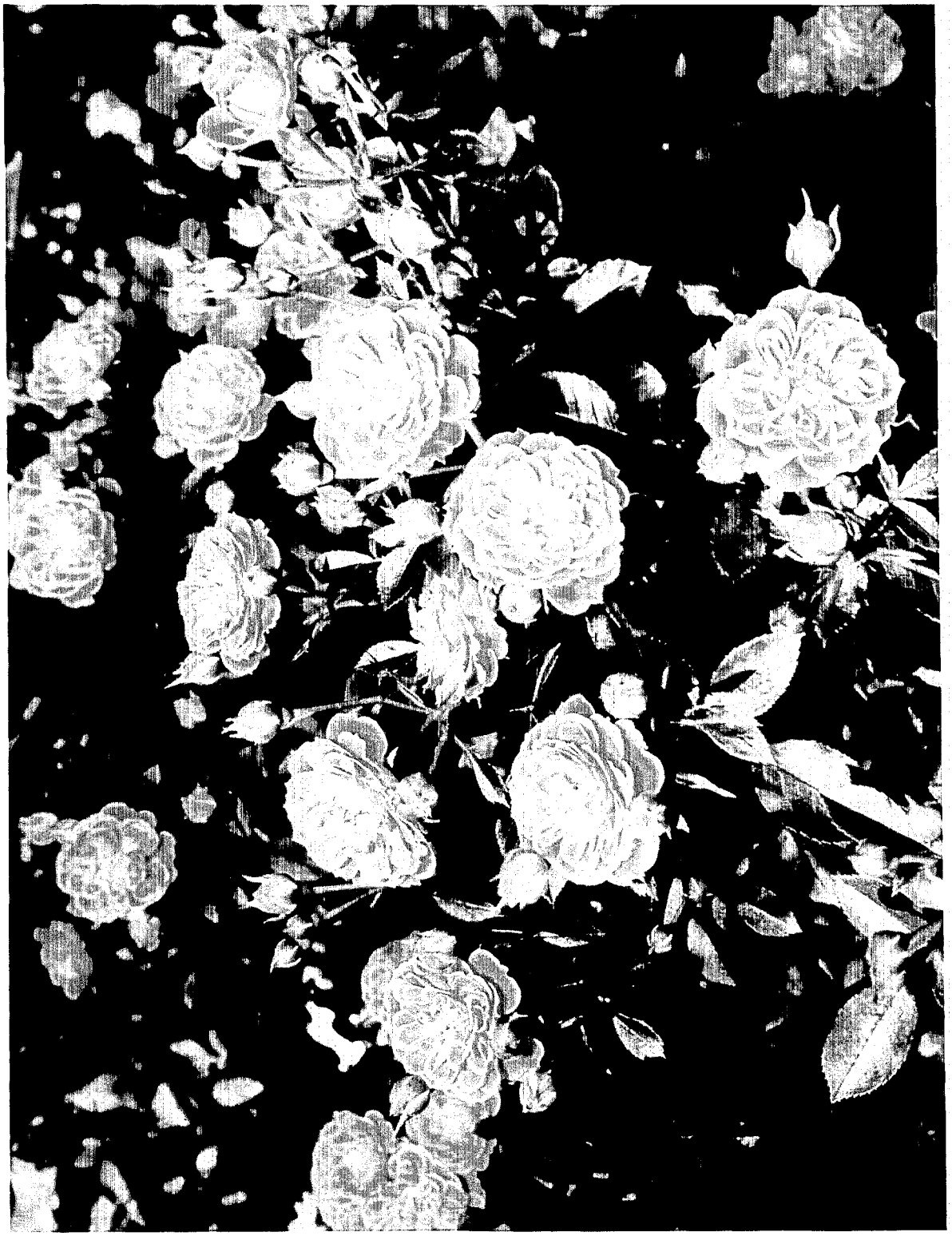

* * * * *